United States Patent [19]
Chapelon et al.

[11] Patent Number: 6,071,238
[45] Date of Patent: Jun. 6, 2000

[54] THERAPY PROBE

[75] Inventors: Jean-Yves Chapelon, Villeurbanne; Emmanuel Blanc, St. Genis Laval; François Lacoste, Rueil Malmaison, all of France

[73] Assignees: Technomed Medical Systems, Vaux en Verlin; Insern, Paris Cedex, both of France

[21] Appl. No.: 08/884,336

[22] Filed: Jun. 27, 1997

[30] Foreign Application Priority Data

Jun. 28, 1996 [FR] France .................................. 96 08096

[51] Int. Cl.⁷ .......................... A61B 17/22; A61B 08/12
[52] U.S. Cl. ................................ 600/439; 601/2
[58] Field of Search .................... 600/437, 439, 600/459, 115, 116, 121, 124; 604/22; 607/96, 97; 601/2

[56] References Cited

U.S. PATENT DOCUMENTS

| | | |
|---|---|---|
| 4,858,613 | 8/1989 | Fry et al. |
| 5,115,814 | 5/1992 | Griffith et al. |
| 5,471,988 | 12/1995 | Fujio et al. |
| 5,558,672 | 9/1996 | Edwards et al. |
| 5,676,151 | 10/1997 | Yock |
| 5,720,286 | 2/1998 | Chapelon et al. |
| 5,720,287 | 2/1998 | Chapelon et al. |
| 5,738,100 | 4/1998 | Yagami et al. |
| 5,762,066 | 6/1998 | Law et al. |
| 5,810,748 | 9/1998 | Ueberle |

FOREIGN PATENT DOCUMENTS

95/02994   2/1995   WIPO .

*Primary Examiner*—Marvin M. Lateef
*Assistant Examiner*—Shawna J. Shaw
*Attorney, Agent, or Firm*—Cohen, Pontani, Lieberman & Pavane

[57] ABSTRACT

An ultrasound therapy probe is provided comprising a therapy transducer movably mounted on a probe body, an at least partially deformable flexible casing around the therapy transducer, and a guard ring limiting deformations of the flexible casing when the transducer moves with respect to the probe body. The therapy transducer can be moved between a therapy position and a retracted position, the guard ring constituting an end-of-travel stop against which the therapy transducer bears in a therapy position. This ensures that movements of the organ to be treated are kept to a minimum when the therapy transducer moves with respect to the probe body.

28 Claims, 3 Drawing Sheets

THERAPY PROBE

BACKGROUND OF THE INVENTION

The present invention relates to a therapy probe, comprising a therapy transducer movably mounted on a probe body.

Such probes are notably used for prostate treatment using focused ultrasound, by rectal route. Such probes are also used for treating the oesophagus, the stomach, the liver and, more generally in percutaneous treatment or treatment by laparoscopy.

Such probes advantageously comprise an imaging transducer, enabling the treated region to be visualized during treatment.

WO-A-8907909 discloses a therapy and imaging probe for endocavital use, comprising a therapy transducer which is movable in rotation and an imaging transducer which is movable linearly; the linear and rotational movements are independent.

FR-A-2,673,542 (WO-A-9215523) discloses a therapy and imaging probe, comprising a spoon-shaped therapy transducer with which an imaging transducer is associated. The two transducers do not move with respect to each other.

FR-A-2,708,207 discloses a therapy and imaging probe, comprising a spoon-shaped therapy transducer. The therapy transducer is movable in rotation and the imaging transducer is movable linearly.

FR-A-2,715,822 discloses a therapy and imaging probe in which the therapy transducer and the imaging transducer are movable and are driven by common drive means.

N. Bom et al, "Early and recent intraluminal ultrasound devices", International Journal of Cardiac Imaging, 4:79–88 1989 discloses various types of imaging or treatment probes.

All these therapy probes set out to provide therapy which is as effective and accurate as possible; if an imaging transducer is provided, another aim is to allow the treated region to be visualized, preferably during treatment. Finally, regarding endocavital probes, the total probe volume or cross-section is also an important parameter.

SUMMARY OF THE INVENTION

The invention deals with new problems found with existing probes, and solutions enabling these problems to be resolved. Some of these problems apply to all probes, regardless of whether they include an imaging transducer. Other problems only occur when the probes have a therapy transducer and a imaging transducer.

One problem that has been discovered concerns detecting movements of the patient. The prior art documents cited describe various systems for maintaining and guiding the probe. None of these documents deals with the new problem of patient movement during treatment. Such movements can however lead to the probe moving with respect to the patient, or moving with respect to the organ to be treated or visualized. The invention proposes a solution to this new problem.

Another problem discovered in the framework of the invention involves the guiding and maintaining of the probe with respect to the patient. In international application WO-A-8907909, for prostate treatment, it is proposed to apply a rotary movement about its general axis to the probe introduced into the rectum. In FR-A-2,673,542, for prostate treatment, an endorectal treatment and imaging probe is provided, together with an urethral imaging probe: while the two probes are being put into place, it is proposed to move the probes in the plane of symmetry of the patient to bring them closer or further to/from each other; the relative position of the probes is then "frozen" for treatment. During treatment, the two probes are moved independently of each other in rotation about their respective longitudinal axes and are moved linearly together, along their parallel longitudinal axes, i.e. essentially parallel to the rectum. FR-A-2,708,207 proposes a probe mounted for linear movement in three directions, and in rotation about its longitudinal axis. FR-A-2,715,822 disclose a probe mounted in rotation about its longitudinal axis in a collar fixed to one end of the rod. The other end of the rod is mounted in a swivel joint, allowing rotation in a vertical plane. The swivel joint is mounted for linear movement along two axes, in the same vertical plane.

New problems have now come to light with these devices: firstly, movement in the direction of propagation of the ultrasound waves is not provided for during treatment; in the case of the prostate, one merely moves the probe in the direction of the rectum during treatment. This creates problems in treating the organ accurately and fully.

Secondly, rotating the probe about its longitudinal axis is problematic as this can lead to the organ being treated moving, particularly if the probe does not have a cylindrical cross-section; this is for example the case in FR-A-2,708,207 or yet again in FR-A-2,715,822 when the flexible casing is inflated. This invention proposes a solution to these new problems.

Another problem discovered in the framework of the invention concerns the introduction of the probe. When, for example, treating the prostate by rectal route, it is necessary to introduce the probe into the patient's rectum, which is not rectilinear. This problem also occurs with endocavital, percutaneous or laparoscopic treatment of other organs, such as for example the stomach or the liver where the probe must also be introduced through an opening which is not necessarily rectilinear. Prior art probes do not provide any solution to this problem, which is not mentioned in the cited documents.

Yet another problem discovered in the framework of the invention involves movements of the probe with respect to the organ to be treated. As mentioned above, rotation of the probe about its longitudinal axis creates problems as it can lead to the organ to be treated moving, particularly if the probe does not have a cylindrical cross-section. This particular problem does not occur in the case of the probe disclosed in FR-A-2,715,822, in which the therapy transducer and the imaging transducer are arranged inside a rigid and cylindrical probe body; however, this solution increases probe diameter or decreases the size of the therapy transducer. The invention provides a solution to this new problem without however involving a reduction in therapy transducer size or an increase in probe cross-section.

The invention provides a solution to the new problem of relative movements between the probe and the organ being treated, when the therapy transducer moves with respect to the probe.

These new problems occur with all types of probes, whether they be intended for use in therapy, therapy and imaging, or even simply for imaging.

Finally, the invention provides a solution to the new problem of relative movements of the therapy transducer, inside a restricted space, and without involving movement of the organs to be treated or a reduction in the size of the therapy transducer.

All these new problems are resolved by the invention which provides a therapy probe comprising a therapy transducer movably mounted on a probe body, an at least partially deformable flexible casing around the therapy transducer, and a guard ring limiting deformations of the flexible casing when the transducer moves with respect to the probe body.

In one embodiment, the therapy transducer can be moved between a therapy position and a retracted position, the guard ring constituting an end-of-travel stop against which the therapy transducer bears in a therapy position.

Means for maintaining the transducer in a therapy position, against the guard ring, can be provided. The guard ring can have an annular shape, surrounding the therapy transducer in a therapy position or the shape of a disc substantially covering the therapy transducer in a therapy position.

The guard ring can be mounted on the probe body or on a support for the probe body.

In another embodiment, a probe is provided comprising an imaging transducer movably mounted on a probe body, the therapy transducer being movable between a therapy position and a retracted position, and the imaging transducer being movable between a retracted position and an imaging position at which the therapy transducer is in a retracted position. The therapy transducer can change from a therapy position to a retracted position under the action of the imaging transducer, when the imaging transducer passes from a retracted position to an imaging position, the therapy transducer changing from its retracted position to its therapy position under the action of recall means when the imaging transducer changes from an imaging position to a retracted position.

The imaging transducer is preferably movable with a linear movement, parallel to a longitudinal axis of the probe and the imaging transducer is movable with a linear movement, along an axis substantially perpendicular to a longitudinal axis of the probe.

The therapy transducer can be movable in rotation about an axis substantially parallel to the longitudinal axis of the probe and, in one embodiment, has a recess for receiving the imaging transducer in its retracted position. The the recess can be provided by milling a side of the therapy transducer closest to the probe body.

The recall means comprise thin plates forming recall springs or can comprise a torsion spring.

The probe can mounted on a ball joint.

The therapy probe can be mounted on means for driving it linearly in a direction substantially perpendicular to a main direction of propagation of therapy waves, and substantially perpendicular to a longitudinal axis of the probe.

The therapy probe can advantageously be mounted on means for driving it linearly in three mutually perpendicular directions, the drive means having clutch means allowing manual drive in at least one plane.

The probe can be mounted on displacing means adapted to move the probe in different directions, with a pitch which is different in the different directions.

The probe can also comprise circulating means adapted for circulating liquid inside the flexible casing, the liquid being preferably under thermostatic control. The circulation means can comprise at least two channels disposed in the probe body.

The invention also provides a method for detecting patient movement, the patient being maintained on a treatment table, consisting in providing a light barrier between the patient and the table. The light barrier can consist of a light transmitter/receiver fixed to the table.

Other features and advantages of the invention will become more clear from the description that follows of various embodiments, provided solely by way of example, and with reference to the attached drawings.

DETAILED DESCRIPTION OF PREFERRED EMBODIMENTS

In all the drawings, therapy probes are shown which include, apart from the therapy transducer, an imaging transducer. The invention also applies when the probe only has a therapy transducer, as explained with reference to FIGS. 9 to 11.

Figure 1:
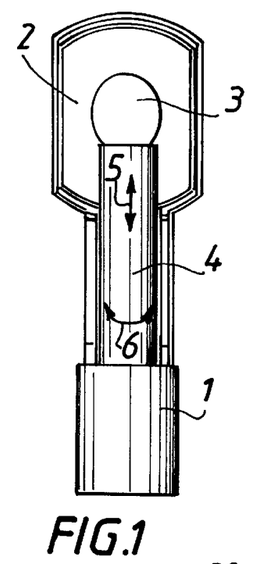
FIG. 1 is a front view of a probe according to a first embodiment of the invention in the imaging position.

FIG. 1 is a front view of a probe according to a first embodiment of the invention in the imaging position, FIG. 1 only shows the forward end of the probe. On FIG. 1 the extremity of a probe body 1, a therapy transducer 2 and an imaging transducer 3 can be recognized.

Figure 2:
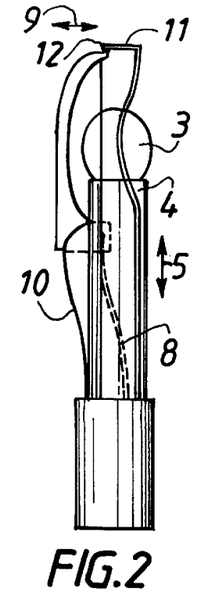
FIG. 2 is a side view of the probe in FIG. 1, in the imaging position.
Figure 3:
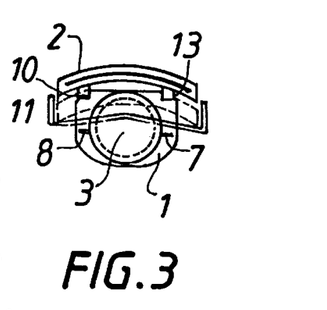
FIG. 3 is a top view, in section, of the probe in FIG. 1, in the imaging position.
Figure 4:
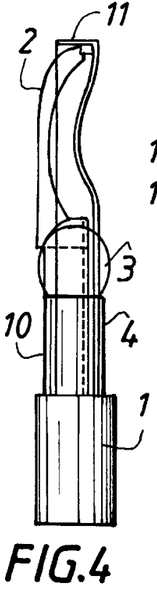
FIG. 4 is a side view of the probe in FIG. 1, in the tiring position.

The therapy transducer 2 is movable with respect to probe body 1, between a therapy or firing position, see FIG. 4, and a retracted position, see FIG. 2, allowing imaging. Therapy Transducer 2 is mounted on the probe body on thin plates 7, 8 which are flexible in a plane perpendicular to the plane of FIG. 1; thus, the therapy transducer is able to move linearly substantially perpendicular to the plane of the figure, i.e. substantially perpendicular to the longitudinal axis of the probe. The therapy transducer is mounted on the probe body by four thin flexible plates situated at both sides of imaging probe support 4, ahead thereof—thin plates 7 and 8, and to the rear thereof—thin plates 10 and 13, on FIGS. 2 and 3.

Imaging transducer 3 is mounted on a support 4 able to move linearly with respect to probe body 1, as indicated by the arrow 5, between a retracted position, see FIG. 4, and an imaging position, see FIGS. 1 or 2. In one embodiment, the imaging transducer is also mounted so as to be movable in rotation, about an axis parallel to the longitudinal axis of the probe, so as to perform a sweep in a transverse plane perpendicular to the longitudinal axis of the probe, as indicated by the arrow 6. One thus ensures the possibility of completely sweeping the region to be treated. Rotation of the imaging transducer can easily be obtained by rotation of support 4.

The therapy transducer is, in the embodiment of FIG. 1, a therapy transducer in the shape of a spoon, of the type disclosed in FR-A-2,673,542 to which reference can be made for more details on this matter. For the imaging transducer, those transducers disclosed in FR-A-2,673,542 or FR-A-2,708,207 can also be used.

FIG. 2 is a side view of the probe in FIG. 1, in the imaging position. On FIG. 2, those elements already described with reference to FIG. 1 can be recognized, as well as the third thin plate 10 supporting the therapy transducer. Arrow 9 shows the direction of movement of the therapy transducer between the firing position and the retracted position.

As can be seen on FIG. 2, in the imaging position, the imaging transducer, via its support 4, pushes the therapy transducer back, to retain the latter in its retracted position.

FIG. 2 also shows a guard ring 11, acting also as a stop, against which the therapy transducer bears in the treatment position. The nature and function of this guard ring will become more clear from the description of FIGS. 9 and 10. Maintaining means, such as magnets 12 enable the therapy transducer to be maintained in the firing position; the maintaining means can also, if needs be, be employed for detecting the presence of the therapy transducer in the firing position.

FIG. 3 is a top view, in section of the probe in FIG. 1, in the imaging position. In FIG. 3 there is shown, in dotted lines, the firing position of the therapy transducer bearing against guard ring 11. On FIG. 3, the four thin plates 7, 8, 10 and 13 supporting the therapy transducer can be seen.

FIG. 4 shows a side view of the probe in FIG. 1, in the firing position; in this firing position, the imaging transducer is in the retracted position, and the therapy transducer is brought, under the action of the thin flexible plates, into the firing position in which it bears against the guard ring.

The probe in FIGS. 1 to 4 operates as follows: for endocavital use, the imaging transducer is brought to the retracted position by moving support 4 linearly towards the probe body. The transducer is then brought, under the action of the thin flexible plates, towards guard ring 11, into the therapy position shown in FIG. 4. The probe in the invention then has a minimal cross-section, allowing ready introduction into a cavity such as, for example, the rectum of a patient.

Once the probe has been positioned substantially opposite the organ to be treated, the imaging transducer is advanced from its retracted position (FIG. 4) towards its imaging position (FIG. 3). The movement of imaging transducer 3 leads to movement of the transducer from its firing position (FIG. 4) towards its retracted position (FIG. 2). In the embodiment of FIG. 1, the imaging transducer slides along the inner surface of the transducer and exercises a force on the latter in the opposite direction the thin flexible plates forming the recall means.

One can then proceed to visualize the organ to be treated, using the imaging transducer, by turning, as necessary, the support 4 of the imaging transducer. Such visualization allows accurate positioning of the probe.

To proceed with treatment, the imaging transducer is brought back to the retracted position, without moving the probe, and the therapy transducer adopts again, under the action of the recall means, its firing position (FIG. 4). One can then proceed with treatment, while at the same time providing visualization, as explained with reference to FIG. 8. The presence of guard ring 11 ensures that the wall of the organ to be treated stays still during movement of the transducer inside the probe, as explained with reference to FIGS. 10 to 12. One can then change over to the imaging position, then to the firing position, depending on the desired treatment protocol.

All means known to the skilled person may be employed for controlling, or detecting imaging transducer movement, such as stepping motors, rack and pinion, endless screws, jacking means, etc. Similarly, for detecting the position of the therapy transducer, means known to the skilled person may be employed. More details on this subject can be obtained by referring to French applications FR-A-2,673, 542, FR-A-2,708,207 or FR-A-2,715,822.

There has been no mention, in the description with reference to FIGS. 1 to 4, of the means for controlling or driving the imaging and therapy transducers, for which the skilled person can use any known means. Nor has there been a description of the outer flexible casing enveloping the complete transducer and guard ring assembly, which can advantageously be similar to that in FR-A-2,673,542 and FR-A-2,708,207.

Compared to the probes in the cited documents, the probe in FIGS. 1 to 4 combines a small cross-section which is easily introduced into a cavity, with a simplicity of control of the relative movements of the transducers. Indeed, it is no longer necessary to provide independent drive means for the imaging and therapy transducers; this simplifies the structure of the probe and its overall volume. The presence of the guard ring ensures the probe is maintained correctly with respect to the organ to be treated. Displacement of the therapy transducer is more limited than in known solutions, which allows treatment in a more restricted volume, and without moving the organ to be treated and changing over from the firing position to the retracted position, or vice-versa.

In the embodiment of FIGS. 1 to 4, the therapy transducer is mounted on recall means consisting of thin flexible plates. Other recall means such as small rods associated with springs can be employed. Provision can also be made for recall of the transducer from its retracted position to its firing position by means for driving the imaging transducer after the latter has reached its retracted position.

Figures 5, 6, 7, 8:
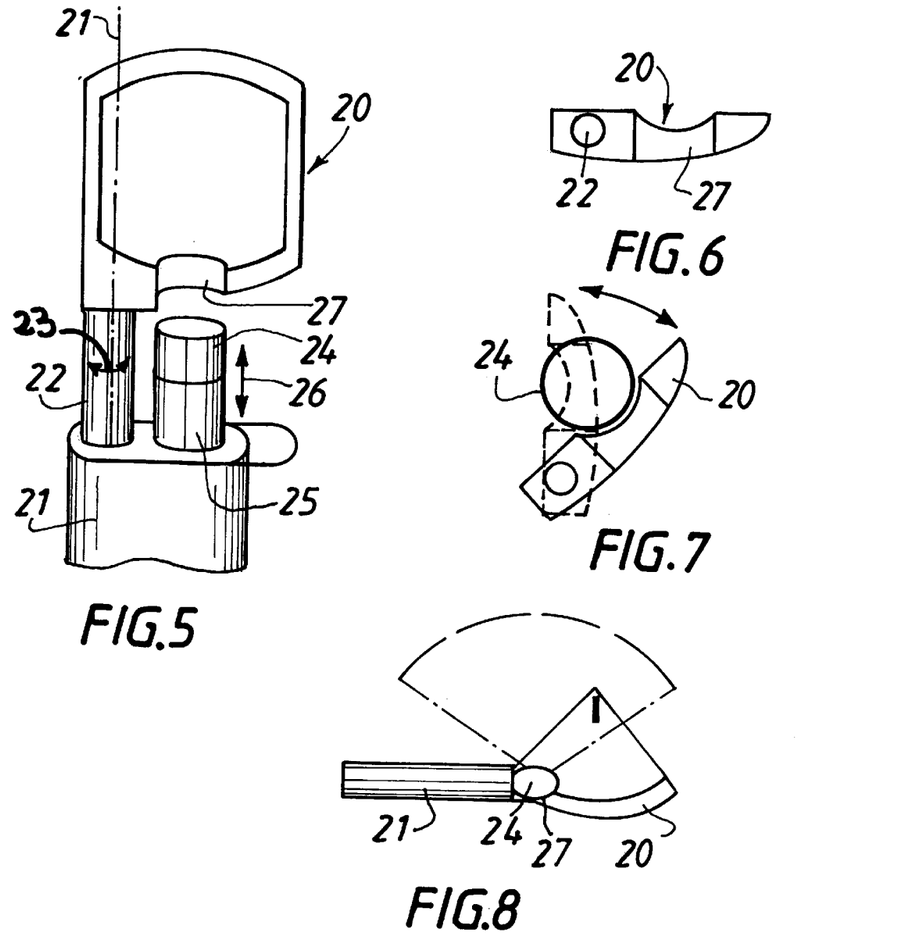
FIG. 5 is a front view of a therapy transducer according to a second embodiment of the invention.
FIG. 6 is a bottom view of the transducer in FIG. 5.
FIG. 7 is a bottom view, partially in section, of the therapy transducer of FIGS. 5 and 6, with the corresponding imaging transducer.
FIG. 8 is a side view, partially in section, of the probe according to the invention, in the firing position.

FIG. 5 is a front view of a probe according to a second embodiment of the invention. The therapy transducer 20 of FIG. 5 is movably mounted with respect to a probe body 21, for rotation with respect to shaft 22, as indicated symbolically by arrow 23. Image transducer 24 is mounted on a support 25 able to move linearly with respect to a probe body 21, as shown symbolically by arrow 26.

In the closest portion of probe body 21, and opposite imaging transducer 24, the therapy transducer has a recess 27, provided, for example, by milling, to facilitate passage of the imaging transducer.

FIG. 6 is a bottom view of transducer 20 in FIG. 5. On FIG. 6, shaft 22 and the milling 27 can be recognized. Transducer 20 has the shape of a self-focusing "spoon", as described in FR-A-2,673,542.

In one embodiment, shaft 22 is controlled in rotation with respect to probe body 21 by drive means, as in French application FR-A-2,673,542. However, in a preferred embodiment, the therapy transducer is not movable independently of the imaging transducer, and is simply urged by recall means. For example, shaft 22 is rotatably mounted in the body 21 over a limited angular range, and is urged by a torsion spring towards one of the extreme positions of the angular range, corresponding to the firing position.

FIG. 7 is a bottom view, in partial section, of therapy transducer 20 and imaging transducer 24 of FIGS. 5 and 6, in the imaging position. On FIG. 7, transducer 20 is shown in solid lines in its retracted position, and in dotted lines in its firing position. The imaging transducer is shown in solid lines in its imaging position; the retracted position is not shown as it is not in the plane of the cross-section.

FIG. 8 is a side view of the probe in the second embodiment of the invention, in partial section and in the firing position. As can be seen on FIG. 8, in the firing position imaging transducer 24 is situated inside the recess 27, on the lower portion of therapy transducer 20.

Operation of the probe according to the second embodiment is similar to that of the probe disclosed in FR-A-2,708,207 except for the following points.

Firstly, it is not necessary to provide drive means for the therapy transducer 20. The therapy transducer 20 changes from its firing position to its retracted position due to the action of the imaging transducer, when the latter changes from its retracted position to its imaging position. More precisely, when the imaging transducer changes from its rectracted position to the imaging position, it urges the transducer back, being opposed by the recall means. When the imaging transducer is brought to the retracted position, the recall means bring the transducer back to the firing position. Thus, the advantages of simplicity of structure and operation, already described with reference to the first embodiment of the invention, are obtained.

Secondly, the presence of recess 27 enables the retracted position of the image transducer to be close to the transducer, as shown in FIG. 8; thus, with respect to the probe in FR-A-2,708,207, the invention allows better observation of the organ to be treated using the imaging transducer, even during treatment. This appears in FIG. 8 where the regions exposed by the therapy transducer and by the imaging transducer are shown diagrammatically. Furthermore, the recess limits the angular amplitude of the movement of the therapy transducer, allowing treatment to be done in a more restrictive volume, and avoids moving the organ to be treated. Finally, in the case of treatment of the prostate, if the imaging transducer in its retracted position is too far from the transducer, as can be the case with the probe in FR-A-2,708,207, it comes to be situated at anus level, in other words opposite tissue which is barely transparent to ultrasound. This is avoided thanks to the recess according to the invention.

Obviously, each of the two aspects of the invention—recall means for the transducer or recess in its lower portion—may be implemented independently of the other. One can also provide a recess or milling also in the embodiment of FIGS. 1 to 4, or do without the recess in the embodiment of FIGS. 5 to 8.

Figure 9:
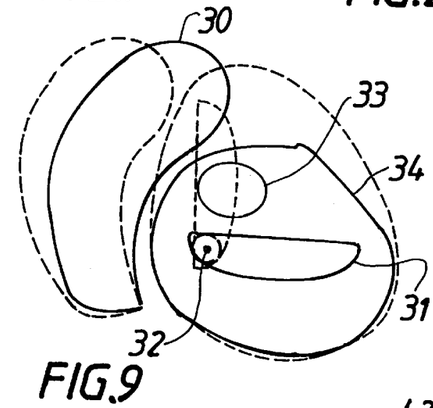
FIG. 9 shows a prior art probe, diagrammatically and in section, in the firing position and the imaging position.

FIG. 9 is a diagrammatical view in section of a prior art probe, in the firing position and the imaging position; the section is in a plane substantially perpendicular to the longitudinal axis of the probe, and containing the organ to be treated. FIG. 9 shows the probe according to FR-A-2,708,207, in solid lines in the imaging position and in dotted lines in the firing position. The organ to be treated 30, for example the prostate for treatment by rectal route, will be recognized together with therapy transducer 31, movable about shaft 32, imaging transducer 33, and the flexible casing or balloon enveloping the probe. As explained in the above-cited documents, the balloon is inflated with a liquid such as degassed water, in order to come into contact with the wall of the organ to be treated and ensure passage of the ultrasound. In the imaging position, the practitioner locates the prostate, draws or designates the contours of the region to be treated; and then changes to the firing position. In the firing position the imaging transducer is retracted into the probe body, and the therapy transducer is swung through 90° around shaft 32, to come opposite the organ to be treated in the position shown in dotted lines on FIG. 9. As shown in FIG. 9, because of the movement of the transducer, it is possible that the organ to be treated will not exactly occupy the same position in the firing and imaging positions in the case of the known probe; this leads to location errors and the danger of treating healthy regions, or of not treating unhealthy regions. In the case of prostate treatment, there are consequently dangers of burning the rectal wall.

The invention proposes a solution to this newly-discovered problem.

It is clear that the problem is not only posed when the probe includes movable therapy and imaging transducers. It also arises when the probe only includes a movable therapy transducer; this can for example be the case where there is provision for sweeping the target, even if the probe does not include an imaging transducer.

Figure 10:
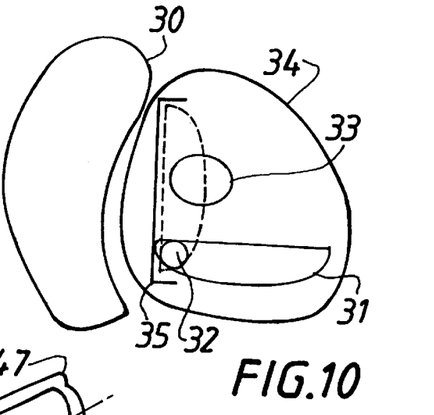
FIG. 10 is a diagrammatical view, in section, of a probe according to a third embodiment of the invention in the firing and imaging position.

FIG. 10 is a diagrammatical view in cross-section of a probe according to a third embodiment of the invention, in the firing position and in the imaging position; this view corresponds to that in FIG. 9 and illustrates the solution provided by the invention to the new problem set out with reference to FIG. 9. Reference numerals that are identical to those in FIG. 9 represent identical or corresponding elements.

According to the invention, the probe has a guard ring 35, which maintains the organ to be treated 30, and a small balloon or envelop 34 in the same position when the therapy transducer 31 and imaging transducer 33 are moved to change from the imaging position to the therapy position and vice-versa. Guard ring 35 makes it possible to avoid movement of the organ to be treated, ensures that the relative position of the probe and the organ to be treated stays the same, regardless of whether the probe is in the firing position or the treatment position. More precisely, the guard ring limits deformations of the flexible casing or envelope when the therapy transducer moves.

The guard ring is advantageously shaped so as to have a contour close to that of the therapy transducer: this ensures a minimal cross-section for the probe in its firing position, and ensures easy introduction into a cavity. One thus preserves the large surface area for the therapy transducer, like in FR-A-2,708,207, without needing to increase the size of the probe.

Figure 11:
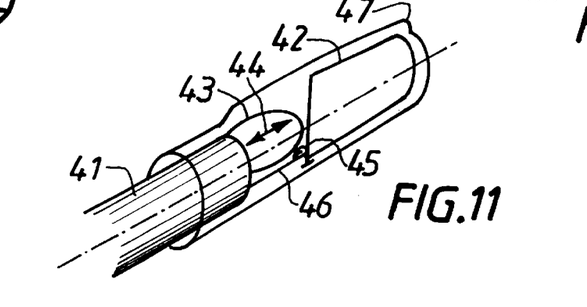
FIG. 11 is a diagrammatical view of a forth embodiment of the invention.

The guard ring can have the shape of a ring surrounding the therapy transducer, as its name suggests, and as shown in FIG. 11. In this case, it can be made in any material whatsoever, for example in pressed metal plate and have an outer profile close to that of the therapy transducer, as appears in FIGS. 1 to 4. The guard ring can also have the shape of a disc, having, at least at its center, an acoustically-transparent window allowing therapy or imaging waves to pass through. The guard ring can for example be made of metal, or any other sufficiently rigid material which ensures the organ is appropriately held. In this case, it is possible for the flexible casing or balloon to only extend to the back of the guard ring, the guard ring itself constituting the wall of the probe in contact with the organ to be treated. This avoid even further a possible movement of the organ to be treated when the flexible casing is deflated. In such a case, the flexible therapy transducer casing is only partially deformable on the same side of the guard ring as the transducer. One can also provide for the flexible casing to be fixed to the guard ring.

FIG. 11 is a diagrammatical view of the fourth embodiment of the invention; on FIG. 11 there can be seen the probe body 41, therapy transducer 42, imaging transducer 43; arrow 44 shows linear movement of the imaging transducer along an axis parallel to the longitudinal axis of the probe and arrow 45 shows the movement of the therapy transducer, rotating about shaft 46.

In the embodiment of FIG. 11, guard ring 47 has the general shape of a ring the contour of which is substantially that of therapy transducer 42; guard ring 47 is mounted on the probe support means, and the body of probe 41 can freely rotate with respect to the guard ring. This solution has the advantage of ensuring perfect immobility of the organ to be treated with respect to the guard ring even if the probe body is caused to rotate about its longitudinal axis to provide a lateral sweep during therapy.

Figure 12:
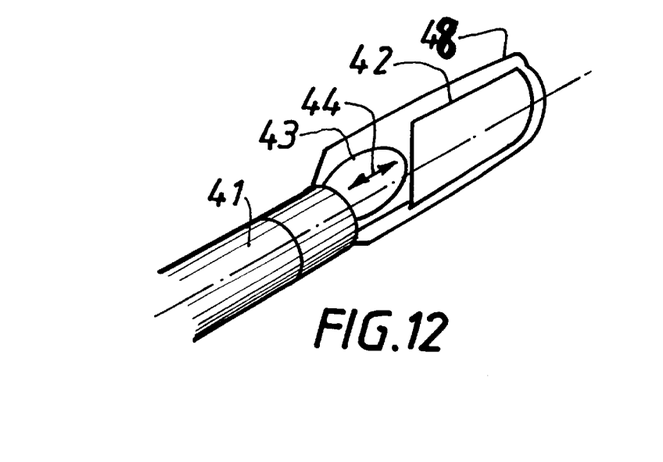
FIG. 12 is a diagrammatical view of a fifth embodiment of the invention.
Figure 13:
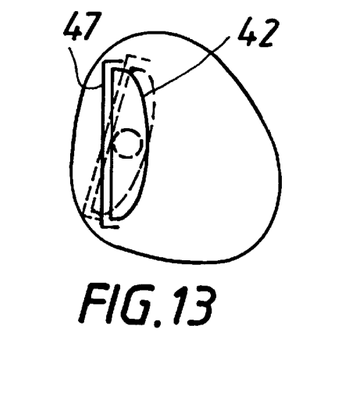
FIG. 13 is a diagrammatical view of the fifth embodiment of the invention, in section like in FIGS. 9 and 10.

FIG. 12 is a diagrammatical view of a fifth embodiment of the invention; this embodiment is substantially identical to the one in FIG. 11, except for the fact that guard ring 48 is mounted on the forward end of the probe body. This solution has the advantages of great simplicity of implementation, and of ensuring minimal cross-section for the probe. It is however possible, in this case, that the organ to be treated will move slightly if the probe body is caused to rotate about its longitudinal axis for providing a lateral sweep in therapy, as shown on FIG. 13 in solid lines and dotted lines. This movement is in any case of a considerably limited amplitude when compared to the movements that are possible in the prior art solution described with reference to FIG. 9.

Obviously, the solution of the invention can be implemented with other embodiments of the invention alone or in combination. Thus, a guard ring can be provided in the first embodiment of the invention as shown on FIGS. 1 to 4; one could also omit it, in view of the limited movements of the therapy transducer in this embodiment. In the second embodiment of the invention, a guard ring can also advantageously provided, even if angular displacement of the therapy transducer is limited.

The presence of a guard ring is particularly advantageous when, as explained with reference to FIGS. 1 to 8, the therapy transducer is mounted on recall means and changes from its therapy position to its retracted position under the action of the imaging transducer when the latter changes from its retracted position to its imaging position. When the imaging transducer is retracted, the guard ring can act as an end-of-travel stop for the therapy transducer, thereby ensuring accurate positioning. One can also provide means for maintaining the therapy transducer on the guard ring, making it possible to maintain the therapy transducer against the guard ring, or, yet again, detection means making it possible to sense the position of the therapy transducer against the guard ring, for enabling firing.

Whatever the case might be, the presence of a guard ring is advantageous when it is necessary to ensure the organ to be treated is maintained in position during movements of a transducer. The guard ring makes it possible to limit the deformations of an at least partially deformable casing or envelope surrounding a movable therapy transducer. One thus ensures the organ to be treated is kept well in position and simultaneously that the probe has minimal cross-section.

Figure 14:
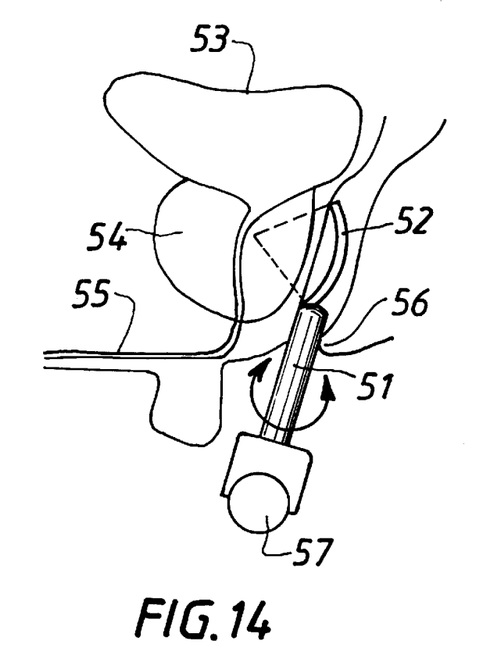
FIGS. 14 and 15 are two diagrammatical views, in section, of probes according to the invention, in position for prostate treatment by rectal route.
Figure 15:
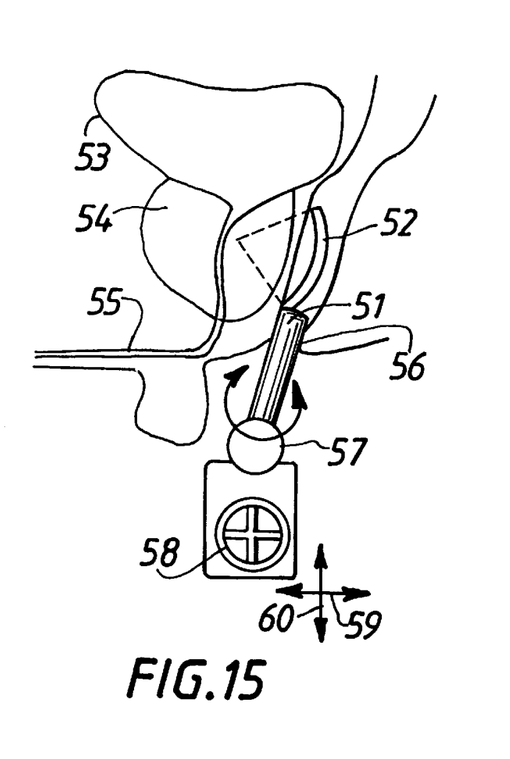

FIGS. 14 and 15 show two diagrammatical views, in cross-section, of probes according to the invention, in a position for treating the prostate by rectal route; on FIGS. 14 and 15, there can be recognized probe 51, with therapy transducer 52, the bladder 53, prostate 54, urethra 55 and rectum 56 of the patient. FIGS. 14 and 15 are top views, the patient being normally in the "gun-dog" lying position on a treatment table, for this type of treatment.

According to the invention, probe 51 is mounted on a ball joint 57, allowing easier introduction into the rectum: thanks to ball joint 57, the probe can be disposed so that its longitudinal axis is precisely parallel to the patient's rectum. One thus avoid wounding the patient and introduction of the probe is facilitated.

As can be seen on FIG. 15, ball joint 57 of probe 51 is advantageously mounted on displacement means 58 making it possible to move the probe linearly along three axes, two of which are shown symbolically by the arrows 59 and 60 on FIG. 15, the third axis being perpendicular to the plane of the figure, in other words to the plane of the treatment table.

The invention thus proposes to notably provide vertical movement of the probe, i.e. movement in a direction transverse to the longitudinal axis of the probe and transverse to the main direction of propagation of the therapy waves.

This movement in a direction perpendicular to the axis of the figures makes it possible to treat larger volumes, while limiting rotation of the probe. Considering the prostate, this movement makes it possible to provide good adjustment of the probe position for treating lobes of the organ, without having to carry out significant movements of the probe in rotation about its longitudinal axis.

Movement may or may not be provided by a motor. Where a motor is employed, motor-driven movement, transversally to the main direction of propagation of therapy waves can be provided to ensure a sweep of the organ to be treated, while avoiding or limiting rotation of the probe body about its axis.

Even if a motor does not provide the movement, such movement nevertheless makes it possible, in the case of large organs, to carry out manual adjustment in the treatment medium, thereby limiting the amplitude of rotation of the probe.

The invention thus makes it possible to preserve, throughout the course of treatment, a treatment field the direction of propagation of which is always substantially perpendicular to the surface of the organ to be treated.

In the plane of FIGS. 14 and 15, i.e. in the plane containing the main direction of propagation of the therapy waves, movement can be motor-driven or not. In one embodiment of the invention movement is provided by a motor, but the probe is also designed to be moved manually. This has the following advantages. Firstly, while introducing of the probe, this enables the practitioner can readily check positioning of the probe, and measure resistance to introduction. This avoids wounding the patient through motor-driven movement of the probe the power of which is not necessarily well controlled and perceived by the practitioner. Secondly, manual movement of the probe makes it possible to constitute a reference so as to then limit movements of the probe provided by the motor. Thus, the initial position, determined manually, corresponds to the mean position, and the motor should not move the probe with respect to this mean position through a distance exceeding a predetermined value.

In one particularly advantageous embodiment of the invention, movement of the probe during treatment is provided, using different displacements in the various directions.

Indeed, a volume can be treated by juxtaposing individual lesions, i.e. individual "shots", by moving the transducer along two sweep directions of the volume to be treated. These two directions are directions generally perpendicular to the direction of propagation of the beam, and correspond to a mode of treatment in which the volume is treated by successive planes which are substantially perpendicular to the direction of propagation of the waves.

This mode of treatment involves the following new problem: it is possible that the therapy transducer will generate an asymmetrical beam, notably if it has a rectangular shape or a shape similar to that in FIG. 1. In this case, due to the lack of symmetry of the ultrasound beam, use of a constant pitch to juxtapose the lesions in the two directions will lead either to lesions being superimposed over each other in one direction, or to an intermediate untreated region in the other direction.

The ultrasound beam is not necessarily symmetrical, depending on the shape of the transducer; in the case of a rectangular shape for the therapy transducer, the lesions produced at the focus are consequently elliptical in cross-section, the smallest diameter corresponding to the largest width of the transducer.

To resolve this new problem, particularly for transducers having an elongated focal spot such as rectangular transducers, the invention proposes to adapt the fire pitch to shape of the lesion. For example, considering a rectangular transducer of size 50 mm×35 mm, the optimum fire pitch is 1.6 mm in the longitudinal direction, and 2.3 mm in the lateral direction.

The invention thus proposes that the means for moving the probe provide such movement with a different pitch in the various directions.

Figure 16:
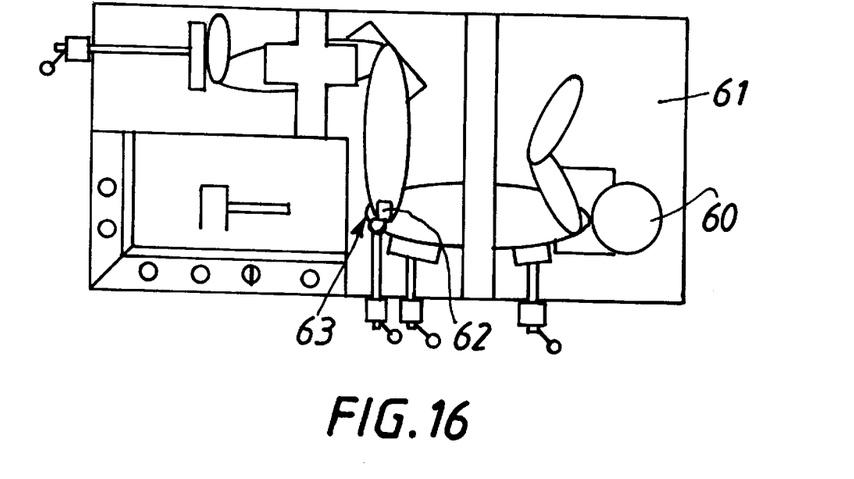
FIG. 16 is a diagrammatical view showing a patient in the position for treatment with a probe according to the invention.

In FIG. 16 is a diagrammatical plan view of a patient in position for treatment with a probe according to the invention. FIG. 16 shows the patient 60, on a treatment table 61, supported if necessary by cushions. The patient is prevented from moving by straps or adjustable spacers. Despite this, it is possible that the patient will move during the course of treatment. There is then a danger of shifting the probe with respect to the patient, leading to incomplete or inappropriate treatment.

To warn the practitioner of this and to allow him to check suitability of treatment, the invention proposes providing the patient with a light barrier, making it possible to detect patient movement. For this, there is fixed, for example on the patient's hip, a reflector 62, and a transmitter/receiver 63 is provided on treatment table 61 or on a point that is fixed with respect to the table. For the reflector or transmitter/receiver, elements known to the skilled man may be employed. The light barrier in FIG. 16 is arranged in a plane perpendicular to the plane of the treatment table for detecting movements of the patient in the direction of the treatment table. These movements are, in effect, those encountered most frequently.

The invention makes it possible to ensure the patient's position is maintained well, and one can then consider that the organ to be treated—here the prostate—is fixed in space. This makes it possible to employ a probe mounted on a drive unit, which is fixed with respect to the treatment table. One can thereby accurately control movements of the probe with respect to the organ to be treated.

The invention obviously does not only apply to treatment, but also to periods before and after treatment, separate from the actual treatment phase. It can also simply be applied to imaging, and the term "treatment table" does not imply that the patient is necessarily undergoing treatment when the invention is applied. The invention is thus not a method for therapeutic treatment of the human body.

In another advantageous embodiment, the probe of the invention includes means for circulating the liquid used for inflating the flexible casing surrounding the therapy transducer. These circulation means comprise, for example, at least two channels provided in the probe body, allowing the coupling liquid filling the flexible casing to circulate. The probe is then connected to a circulation pump and to a liquid reservoir or to equivalent means.

Compared to solutions in the cited prior art, in which a single flexible casing inflation channel is provided, the invention makes it possible, thanks to circulation of the liquid, to evacuate bubbles that eventually form during treatment and/or to allow cooling of the transducer(s) and/or the wall of the organ to be treated.

Indeed, bubbles can form in the liquid, due to heating of the liquid or due to cavitation effects resulting from the waves sent from the transducer. Circulation of the liquid makes it possible to limit bubble formation, thereby improving the effectiveness of treatment and limiting probe heating.

Advantageously, the liquid is provided with thermostatic control: circulating the thermostatically-controlled liquid can constitute a simple and effective way of cooling the therapy transducer or the imaging transducer. Fluid circulation also makes it possible to cool, or maintain at a low temperature, that part of the organ to be treated in contact with the probe. This limits surface burns of the patient; in the case of prostate treatment, burning of the rectal wall is avoided.

Obviously, the preferred embodiments of the invention may be subject to variations: the various features of the various embodiments described can be combined or used alone, depending on requirements.

Application of the probe to prostate treatment is only one example of possible treatments. The probe of the invention can also be used for the treatments mentioned above.

What is claimed is:

1. A therapy probe for use in a body cavity comprising a therapy transducer mounted on a support and movable with respect to a probe body between a therapy position and a retracted position; an at least partially deformable flexible casing around said therapy transducer; and a guard ring for limiting deformations of said flexible casing in front of said transducer when the transducer is moved with respect to the probe body from the therapy position to the retracted position.

2. The probe according to claim 1, wherein said therapy transducer can be moved between a therapy position and a retracted position, said guard ring constituting an end-of-travel stop against which said therapy transducer bears in a therapy position.

3. The probe according to claim 2, having means for maintaining said transducer in a therapy position, against said guard ring.

4. The probe according to claim 2, wherein said guard ring has an annular shape, surrounding said therapy transducer in a therapy position.

5. The probe according to claim 2, wherein said guard ring has the shape of a disc substantially covering said therapy transducer in a therapy position.

6. The guard ring according to claim 1, wherein said guard ring is mounted on said probe body.

7. The probe according to claim 1, wherein said guard ring is mounted on a support for said probe body.

8. The probe according to claim 1, comprising an imaging transducer movably mounted on said probe body, said therapy transducer being movable between a therapy position and a retracted position, and said imaging transducer being movable between a retracted position and an imaging position at which said therapy transducer is in a retracted position.

9. The probe according to claim 8, wherein said imaging transducer is movable with a linear movement, parallel to a longitudinal axis of said probe.

10. The probe according to claim 8, wherein said imaging transducer is movable with a linear movement, along an axis substantially perpendicular to a longitudinal axis of said probe.

11. The probe according to claim 8, wherein said therapy transducer is movable in rotation about an axis substantially parallel to the longitudinal axis of said probe.

12. The probe according to claim 8, wherein said therapy transducer has a recess for receiving said imaging transducer in its retracted position.

13. The probe according to claim 12, wherein said recess is provided by milling a side of said therapy transducer closest to said probe body.

14. The probe according to claim 1, comprising an imaging transducer movably mounted on said probe body, said therapy transducer being movable between a therapy position and a retracted position, and said imaging transducer being movable between a retracted position and an imaging position at which said therapy transducer is in a retracted position, said therapy transducer changing from a therapy position to a retracted position under the action of said imaging transducer, when the imaging transducer passes from a retracted position to an imaging position and said therapy transducer changing from its retracted position to its therapy position under the action of recall means when said imaging transducer changes from an imaging position to a retracted position.

15. The probe according to claim 14, wherein said imaging transducer is movable with a linear movement, parallel to a longitudinal axis of said probe.

16. The probe according to claim 14, wherein said imaging transducer is movable with a linear movement, along an axis substantially perpendicular to a longitudinal axis of said probe.

17. The probe according to claim 14, wherein said recall means comprise thin plates forming recall springs.

18. The probe according to claim 14, wherein said therapy transducer is movable in rotation about an axis substantially parallel to the longitudinal axis of said probe.

19. The probe according to claim 14, wherein said recall means comprise a torsion spring.

20. The probe according to claim 14, wherein said therapy transducer has a recess for receiving said imaging transducer in its retracted position.

21. The probe according to claim 20, wherein said recess is provided by milling a side of said therapy transducer closest to said probe body.

22. The probe according to claim 1, wherein said probe is mounted on a ball joint.

23. The probe according to claim 1, mounted on means for driving it linearly in a direction substantially perpendicular to a main direction of propagation of therapy waves, and substantially perpendicular to a longitudinal axis of the probe.

24. A probe according to claim 1, mounted on means for driving it linearly in three mutually perpendicular directions, said drive means having clutch means allowing manual drive in at least one plane.

25. The probe according to claim 1, wherein it is mounted on displacing means adapted to move said probe in different directions, with a pitch which is different in said different directions.

26. The probe according to claim 1 comprising circulating means adapted for circulating liquid inside said flexible casing.

27. The probe according to claim 26, wherein said liquid is under thermostatic control.

28. The probe according to claim 26, wherein said circulation means comprise at least two channels disposed in said probe body.

* * * * *